(12) United States Patent
Lane et al.

(10) Patent No.: US 8,177,723 B2
(45) Date of Patent: May 15, 2012

(54) FILTER FOR BLOOD PRESSURE MONITOR

(75) Inventors: John A. Lane, Weedsport, NY (US); Scott A. Martin, Warners, NY (US); William J. Smirles, Deerfield, IL (US); Braxton Lathrop, Lake Oswego, OR (US); Andrew M. Robottom, Beaverton, OR (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 1291 days.

(21) Appl. No.: 11/834,288

(22) Filed: Aug. 6, 2007

(65) Prior Publication Data
US 2009/0043238 A1      Feb. 12, 2009

(51) Int. Cl.
*A61B 5/02*      (2006.01)
(52) U.S. Cl. .................................. 600/490; 600/498
(58) Field of Classification Search .................. 600/490; 454/235, 244, 252, 187
See application file for complete search history.

(56) References Cited

U.S. PATENT DOCUMENTS

| | | | | |
|---|---|---|---|---|
| 3,274,989 A | * | 9/1966 | Jenson et al. | 126/110 R |
| 5,314,516 A | * | 5/1994 | Kashima | 55/484 |
| 6,450,966 B1 | * | 9/2002 | Hanna | 600/490 |
| 6,666,845 B2 | * | 12/2003 | Hooper et al. | 604/132 |
| 2002/0164944 A1 | * | 11/2002 | Haglid | 454/228 |

* cited by examiner

*Primary Examiner* — Miranda Le
*Assistant Examiner* — Tiffany Weston

(57) ABSTRACT

An automatic blood pressure monitor having a housing containing a first water and air tight chamber and a second air supply chamber, the chambers being separated by a common wall. Pneumatic equipment is mounted in the first chamber having a flow circuit for inflating and deflating a blood pressure cuff. A filtering unit is mounted in the common wall for retaining particulate material and moisture that is exchanged between the two chambers. The flow circuit has an air inlet port and an air exhaust port which are both located adjacent to the filter contained in the filtering unit whereby particulate material and moisture drawn into the flow circuit is retained upon the filter during inflation cycle and the particulate material and moisture retained on the filter is blown back into the air supply chamber during the deflation cycle. A drain is mounted in the floor of the air supply chamber through which particulate material and moisture collected in the chamber is discharged to the surrounding ambient. A restricted opening is provided in an outer wall of the air supply chamber which allows ambient air to enter the chamber through a tortuous path of travel.

7 Claims, 2 Drawing Sheets

FILTER FOR BLOOD PRESSURE MONITOR

FIELD OF THE INVENTION

This invention relates to a blood pressure monitor and in particular to an automatic blood pressure monitor that is protected against the ingress of ambient air that is contaminated with particulate material and moisture.

BACKGROUND OF THE INVENTION

Many blood pressure devices, such as sphyghmomanometers, are adapted to both automatically monitor and measure a patient's blood pressure. In this type of system, a flow circuit is used to inflate and deflate a cuff that is placed over a body extremity of a patient such as a finger, an arm or a leg. The cuff typically is inflated to a predetermined pressure and is then deflated to release the pressure exerted on the extremity. Blood pressure readings are taken, either during the inflation phase of the cycle or the deflation phase, to obtain the patient's systolic and diastolic pressure.

These automatic blood pressure devices oftentimes must be employed under adverse conditions where ambient air is heavily contaminated with particulate materials, water or a combination of both which can find its way into the system through the housing enclosing the system or the air inlet and exhaust ports to the systems flow circuit. As disclosed in U.S. Pat. No. 6,450,966 B1 to Hanna, which discloses an automatic blood pressure measuring system, filters have been employed in prior art systems of this type to prevent contaminants from being carried into the system by the air supply stream entering the flow circuit. The filters used in these prior art systems are relatively small in size and are typically placed inside of the air tubing. In many cases the filters are unable to efficiently block moisture or water from getting to the working components of the system through the flow circuit. When used in a heavily contaminated area or outdoors during periods of heavy fog, rain or snow the filters quickly become clogged producing erroneous pressure readings and eventually the system fails. These prior art devices generally do not place filters at or near the exhaust port of the system and here again dust, dirt, rain, snow and other types of airborne contaminates can pass into the system through the exhaust section of the system to clog valves and contaminate sensors. Lastly, the prior art devices do not provide any means to clean the filters while the blood pressure device is in use. Once a filter becomes clogged, the procedure in progress must be terminated so that the clogged filter can be cleaned or replaced before the procedure can once again be started. Contamination induced failures of automatic blood pressure monitoring and measuring devices are most likely to occur during natural or man made disasters, a time when this kind of information is most needed. In addition, life expectancy of a blood pressure machine that has experienced a number of contaminated related failures can be expected to be foreshortened because of the additional strain that is placed on the working components of the system due to the presence of such contaminants.

SUMMARY OF THE INVENTION

It is therefore a primary object of the present invention to improve automatic non-invasive blood pressure measuring and monitoring equipment.

It is a further object to improve the sealing characteristics of an automatic blood pressure system to better prevent airborne contaminants and water from attacking the working component of the system.

A still further object of the present invention is to provide a means for cleaning an air filter employed in the air system of an automatic blood pressure device.

Another object of the present invention is to extend the usable life of an automatic blood pressure device which is forced to operate for long periods of time under adverse conditions.

These and other objects of the present invention are attained by a device for monitoring blood pressure that has a pneumatic system for inflating and deflating a blood pressure cuff. The system is housed in an enclosed service chamber that is sealed against penetration by air and water. A second air supply chamber is located adjacent to the service chamber with the two chambers sharing a common wall. An air filtering unit is mounted in the common wall which is capable of removing particulate materials and moisture from the air that is exchanged between the compartments. A flow circuit that is associated with the pneumatic system that includes an air inlet port and an air exhaust port, both of which are mounted immediately adjacent to the air filtering unit so that air entering the pneumatic system is cleansed of dirt, dust, water and the like and air that is exhausted from the system is passed back through the filter to dislodge any contaminating materials that have been retained on the filter. The dislodged material is collected in the air supply chamber and is passed out of the chamber via a floor drain.

BRIEF DESCRIPTION OF THE DRAWINGS

For a better understanding of these and other objects of the present invention, reference will be made to the following detailed description of the invention which is to be read in association with the accompanying drawings, wherein.

DETAILED DESCRIPTION

Figure 1:
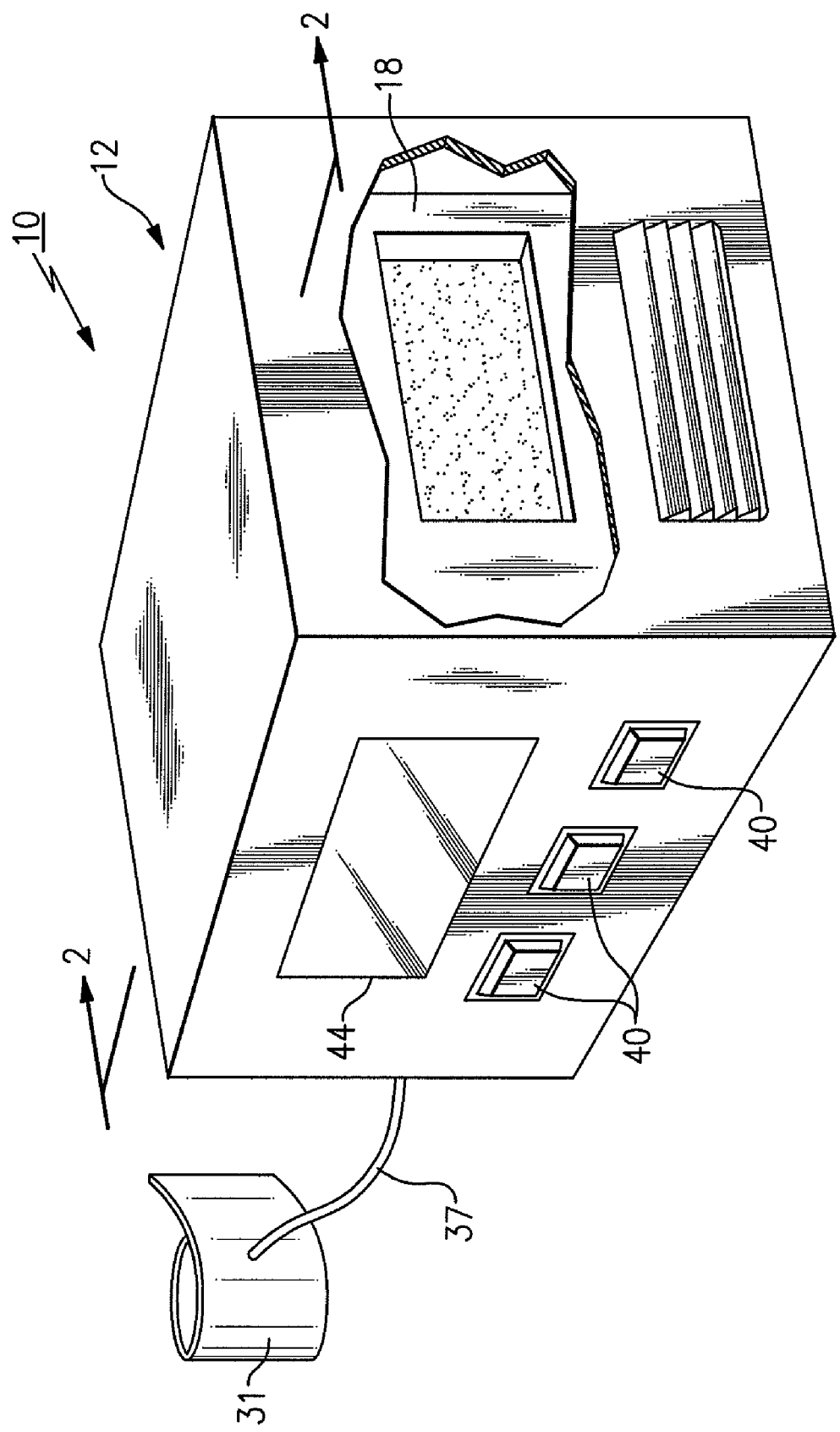
FIG. 1 is a perspective view with portions broken away showing a blood pressure monitor embodying the teachings of the present invention.
Figure 2:
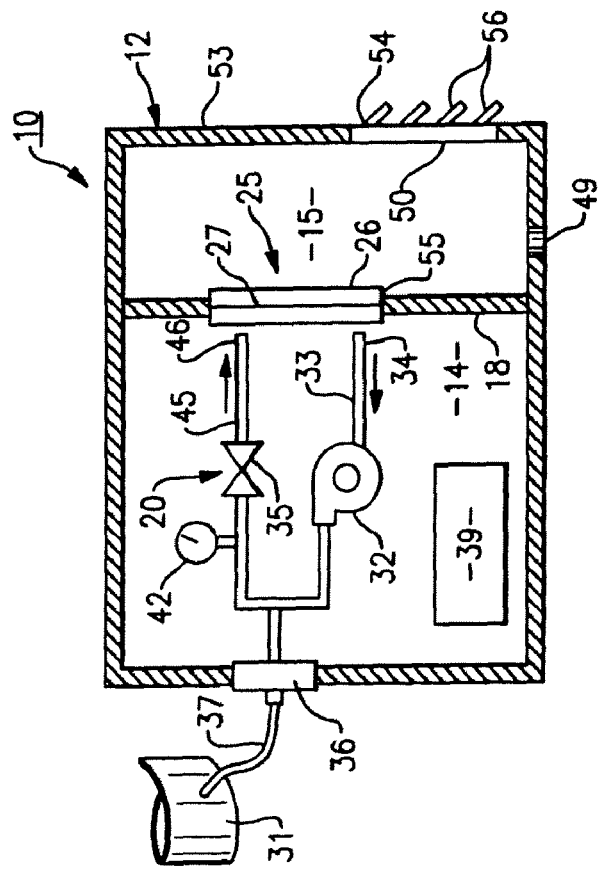
FIG. 2 is a section through the monitor along lines 2-2 in FIG. 1.

The present invention involves an automatic non-invasive blood pressure monitor having the capability of providing a read out of a patient's systolic and diastolic blood pressures. The term blood pressure monitor, as herein used, is broad enough to cover any device that can measure blood pressure and/or store this information in memory for future use. As illustrated in FIGS. 1 and 2, the monitor which is generally referenced 10, includes an enclosed housing 12 that contains a first service chamber or compartment 14 and a smaller air supply chamber or compartment 15. The two chambers are separated by a common interior wall 18.

The service chamber houses a pneumatic air handling system which is shown schematically and is referenced 20 in FIG. 2. An air filtering unit 25 is mounted in the common wall that separates the two chambers. The unit includes a frame 26 and a filter 27 that is centered within the frame. The filter may be fabricated from any suitable material that is known and used in the art for preventing the passage of small size particles of dust and dirt as well as water. Preferably, the filter medium is capable of filtering out particles having a size of one micron or more as well as all moisture that may be contained in the air stream that is passing through the filter.

One example of a suitable material is an expanded polytetrafluoroethylene membrane that is commercially available.

The service chamber is sealed so that no particulate materials, such as dirt, dust or condensate, rain or snow can penetrate the wall or joints of the housing.

The air handling system 20 includes flow circuit for circulating air through the service chamber which is used to inflate and deflate a blood pressure cuff 31. A pump 32 is arranged to draw air into the inlet tube 33 of the flow circuit. The inlet port 34 of the inlet tube is positioned adjacent to and in close proximity with the back face of filter 27. Air is thus drawn from the air supply chamber through the filter by the pump when the cuff is being inflated. At this time, control valve 35 is closed and air is pumped through a connector 36 and lumen 37 into the cuff. When a predetermined inflation pressure is reached, the control valve is opened so that air is bleed out of the cuff to permit systolic and diastolic readings to be taken. The activity of the pump and the control valve are regulated by a microprocessor 39 based on information set into the monitor using control switches 40-40 mounted on the face of the monitor or any other suitable input means. A pressure sensor 42 is also operatively connected into the flow circuit and is arranged to exchange information between the flow circuit and the microprocessor. Data relating to the blood pressure monitoring and measuring procedures is visually displayed on the screen 44 which is also mounted upon the face of the monitor.

The exhaust tube 45 of the flow circuit contains an exhaust port 46 which, like the inlet port 34, is positioned adjacent to and in close proximity with the back face of the filter 27. During the deflation phase of each blood pressure measurement cycle valve 35 is opened and pressurized air that is released from the cuff is blown back through the filter into the air supply chamber thus serving to dislodge any materials including moisture that might have accumulated upon the filter membrane. The dislodged particles and moisture, in turn, fall under the force of gravity in the sump or floor area of the air supply chamber where it is passed out of the chamber via drain 49.

Ambient air is permitted to enter the air supply chamber through an entrance window 50 located in the lower section of the front wall 53 of the housing. Preferably, the top edge 54 of the window is below the level of the bottom edge 55 of the filter frame. The entrance to the window contains a series of horizontally disposed louvers 56-56. Under certain harsh conditions, the monitor may be subjected to high velocity blasts of heavily contaminated air which, if allowed to strike the filter membrane directly, could severely damage the filter and penetrate into the service chamber. As should be now evident, any outside air passing through the air entrance window will have to travel a tortuous path into the air supply chamber and will not be able to contact the filter directly. In addition, the velocity of the incoming air stream will be rapidly disapted.

Figure 3:
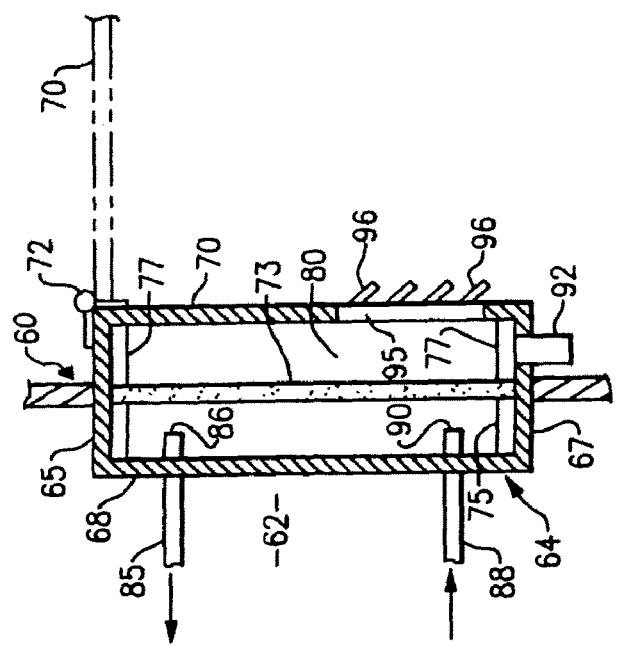
FIG. 3 is a side elevation in section illustrating a filter unit suitable for use in a blood pressure monitor that embodies the teachings of the present invention.

Turning now to FIG. 3, there is illustrated a filter unit, generally referenced 60, that is fitted to an outer wall of a service chamber 62 of a blood pressure monitor of the type described in greater detail above. The unit includes a rectangular frame 64 having a top wall 65 and a bottom wall 67 and a back wall 68 along with two end walls. A panel 70 is mounted by a hinge 72 to the top wall of the frame so that the panel can be moved between a fully opened position as shown in a dotted outline and a fully closed position to enclose the frame. A filter 73 is centrally mounted within the frame. Although not shown, a latch may also be provided to secure the panel tightly against the front of the frame. The filter is removably contained within the frame so that the filter can be removed and replaced when the panel is moved to the open position. In assembly, the filter is vertically aligned within the frame by one or more stops 75 and held in place against the stops by positioners 77-77 that are affixed to the back surface of the front panel. With the filter in place and the panel closed, a front air chamber 80 is established within the frame for supplying air to the service chamber. The inlet tube 85 of the monitor flow circuit is supported in the back wall 68 of the frame to position the inlet port 86 of the flow circuit adjacent to the filter. The exhaust tube 88 of the flow circuit is similarly supported in the back wall of the panel to position the exhaust port 90 of the flow circuit adjacent to the filter. A drain 92 is mounted in the bottom wall of the frame. A restricted air entrance 95 is located in the lower section of the front panel. A series of horizontally disposed louvers 96-96 are adjustably mounted in the panel. Preferably, the louvers are adjustable so that the size of the opening and air flow can be controlled. Here again, the restricted opening is designed to protect the filter from being impacted directly by any high velocity stream of air or water which might force contaminants entrapped in the stream to penetrate the filter membrane.

While the invention has been described with reference to preferred embodiments, it will be understood by those skilled in the art that various changes may be made and equivalents may be substituted for elements thereof to adapt to particular situations without departing from the scope of the invention. Therefore, it is intended that the invention not be limited to the particular embodiments disclosed as the best mode contemplated for carrying out this invention, but that the invention will include all embodiments falling within the scope and spirit of the appended claims.

The invention claimed is:

1. A blood pressure monitor having an enclosed service chamber sealed against the unwanted penetration of dust and water and a filter assembly for permitting air to enter and leave said chamber, wherein said monitor comprises:
    a frame mounted in a wall of said service chamber;
    a filter mounted within said frame for retaining particulate material and water in air that is entering and leaving said service chamber;
    a panel covering the front opening of the frame to establish an air chamber between said panel and said filter;
    a restricted air entrance in said panel of said air chamber for admitting ambient air into said air chamber wherein said air must pass through said restricted air entrance before entering said air chamber.

2. The blood pressure monitor of claim 1, wherein said restricted air entrance further includes a plurality of louvers.

3. The blood pressure monitor of claim 2, wherein the louvers are adjustable.

4. The blood pressure monitor of claim 1, that further includes a bottom wall located in said air chamber and a drain mounted in said floor of said air chamber.

5. The blood pressure monitor of claim 1, wherein said access door is movable between an open and a closed position and wherein said filter is removable from said frame when said access door is in said open position.

6. The blood pressure monitor of claim 1, wherein said service chamber houses a pneumatic system for inflating and deflating said blood pressure cuff, said system further including a flow circuit having an inlet port and an exhaust port positioned adjacent to said filter.

7. The blood pressure monitor of claim 1, wherein said filter is fabricated from a polytetrafluoroethylene material.

* * * * *